United States Patent [19]

Ramanathan

[11] Patent Number: 5,689,443
[45] Date of Patent: Nov. 18, 1997

[54] METHOD AND APPARATUS FOR EVALUATING SCANNERS

[76] Inventor: Naganathasastrigal Ramanathan, 37 Bankview Circle, Rexdale, Ontario, Canada, M9W6S6

[21] Appl. No.: 451,035

[22] Filed: May 25, 1995

[51] Int. Cl.$^6$ .............................. G01B 17/00; A61B 8/00
[52] U.S. Cl. .................. 364/551.01; 364/413.07; 364/413.22; 364/413.25; 364/413.01; 128/660.01; 73/599
[58] Field of Search ................ 364/413.07, 413.22, 364/413.25, 551.01, 413.13, 413.01, 525; 128/660, 660.01, 660.03; 73/599, 602

[56] References Cited

U.S. PATENT DOCUMENTS

| | | | |
|---|---|---|---|
| 4,206,654 | 6/1980 | Keller et al. | 73/620 |
| 4,245,511 | 1/1981 | Soldner | 73/625 |
| 4,331,021 | 5/1982 | Lopez et al. | 73/1 DV |
| 4,433,690 | 2/1984 | Green et al. | 128/660 |
| 4,843,866 | 7/1989 | Madsen et al. | 73/1 DV |
| 4,903,523 | 2/1990 | Flynn | 73/1 DV |
| 5,095,909 | 3/1992 | Nakayama et al. | 128/660.06 |
| 5,107,837 | 4/1992 | Ophir et al. | 128/660.01 |
| 5,178,147 | 1/1993 | Ophir et al. | 128/660.01 |
| 5,293,870 | 3/1994 | Ophir et al. | 128/660.01 |
| 5,339,815 | 8/1994 | Liu et al. | 128/660.01 |

OTHER PUBLICATIONS

Roy C. Preston, The NPL Ultrasound Beam Calibrator, IEEE transactions on Ultrasonics, Ferroelectrics and Frequency control, vol. 35, No. 2, pp. 122–139 Mar. 1988.
Preston et al., Calibration Of Medical Ultrasonic Equipment–Procedures And Accuracy Assesment, IEEE Transactions On Ultrasonics, Ferroelectrics, And Frequency Control, vol. 35, No. 2, pp. 110–121 Mar. 1988.
Lee W. Goldman, M.S. and J. Brian Fowlkes, Ph.D., "Medical CT and Ultrasound: Current Technology and Applications", Published for American Association of Physicists in Medicine, Published by Advanced Medical Publishing, ISBN: 1–883526–03–5, 1995.
Lopez, H., et al., "Methods For Measuring Performance of Pulse–Echo Ultrasound Equipment–Part II: Digital Methods (Stage 1)", Laurel, M.D., American Institute of Ultrasound in Medicine, (AIUM Approved Nov. 15, 1994) in press.
Madsen, E., et al., "Quality Assurance Manual for Gray Scale Ultrasound Scanners" (Stage 2), Laurel MD, American Institute of Ultrasound In Medicine, (AIUM Approved Mar. 2, 1995) in press.
Gammex RMI. (1994), "The Ultrasound QA Cookbook", Middleton, WI, Gammex RMI.
Esko Alasaarela and John Koivukangas, "Evaluation of Image Quality in Ultrasound Scanners in Medical Diagnostics", Journal of Ultrasound in Medicine, vol. 9, p. 23–34, 1990.

(List continued on next page.)

*Primary Examiner*—Emanuel T. Voeltz
*Assistant Examiner*—Hien Vo

[57] ABSTRACT

The apparatus and method for evaluating images for quality assurance parameters of ultrasound image scanners are described. The apparatus includes a digital computer with display output, a video frame grabber or direct image read-out interface from ultrasound scanner, a digital storage, and software. Using a transducer, an ultrasound scanner produces an image, of test objects or phantom, that is temporarily stored in scanner memory. The phantom image is transferred to the memory of the processing computer either by digitizing the video output of the scanner or reading directly by digital means from the scanner. The software enables the user to acquire the image by the above means; associate the images with information on scanner, operator, and expected performance standards and accuracies. As selected by user, the software evaluates scanner performance parameters and produces quantitative results, graphs, and reports for screen display and printer. The processed and inputted information is stored with the measurement set and images for future access. The software generates, using stored and current results, trend graphs of evaluated performance parameters.

20 Claims, 14 Drawing Sheets

OTHER PUBLICATIONS

Paul L. Carson, "Imaging Factors and Evaluation –Ultrasound", In Physics of Medical Imaging: Recording Systems Measurements and Techniques, pp. 366–380, Ed. Arthur G. Haus, American Association of Physicists in Medicine, Pub. American Institute of Physics, 1979.

Albert Goldstein, "Ultrasound Quality Assurance", In Medical Physics of CT and Ultrasound: Tissue Imaging and Characterization, pp. 488–513, Ed. Gary D. Fullerton and James A. Zagzebski.

Medical Physics Monograph No. 6, American Association of Physicists in Medicine, Pub. American Institute of Physics, 1980.

Albert Goldstein, "Evaluating Image Quality in High–Res Ultrasound", Diagnostic Imaging, pp. 89–100, Dec. 1991.

Hector Lopez and Stephen W. Smith, "Implementation of a Quality Assurance Program for Ultrasound B–Scanners", HEW Publication (FDA, USA) 80–8100, 25 Pages, 1979.

K. McCarty, "Test Objects for the Assessment of the Performance of Diagnostic Ultrasound Equipment", In Quality Assurance in Medical Imaging, pp. 77–98, IOP Short Meeting Series No. 2, Institute of Physics, London, 1986.

James A. Zagzebski, "Ultrasound Equipment Acceptance Tests", In Medical Physics of CT and Ultrasound: Tissue Imaging and Characterization, pp. 514–530, Ed. Gary D. Fullerton and James A. Zagzebski, Medical Physics Monograph No. 6, American Association of Physicists in Medicine, Pub. American Institute of Physics, 1980.

Lee W. Goldman, M.S. and J. Brian Fowlkes, Ph.D., "Medical CT and Ultrasound: Current Technology and Applications", Published for American Association of Physicists in Medicine, Published by Advanced Medical Publishing, ISBN: 1-883526-03-5, 1995.

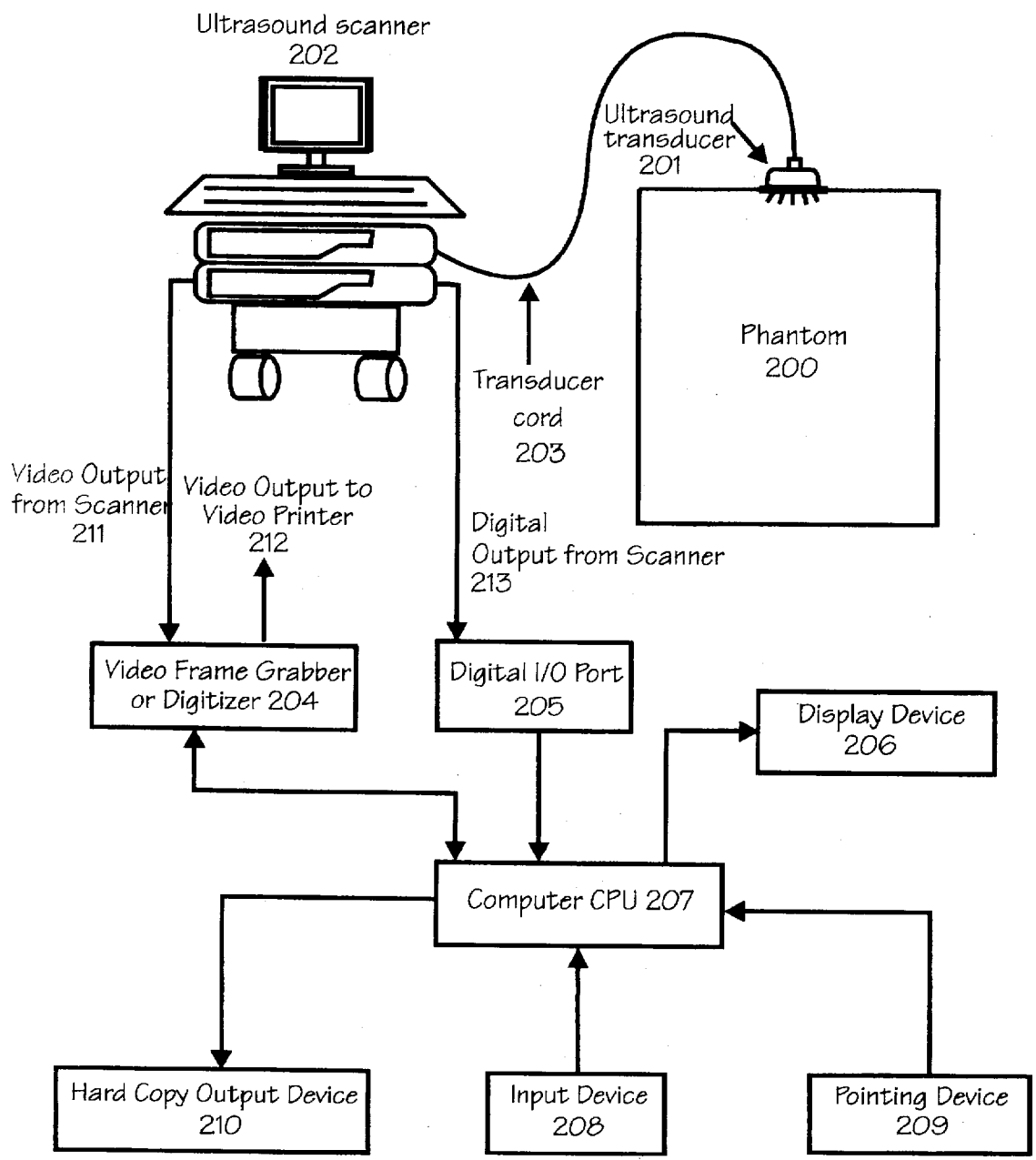
Figure 1. Block Diagram of Typical Apparatus for Evaluating Ultrasound Scanner

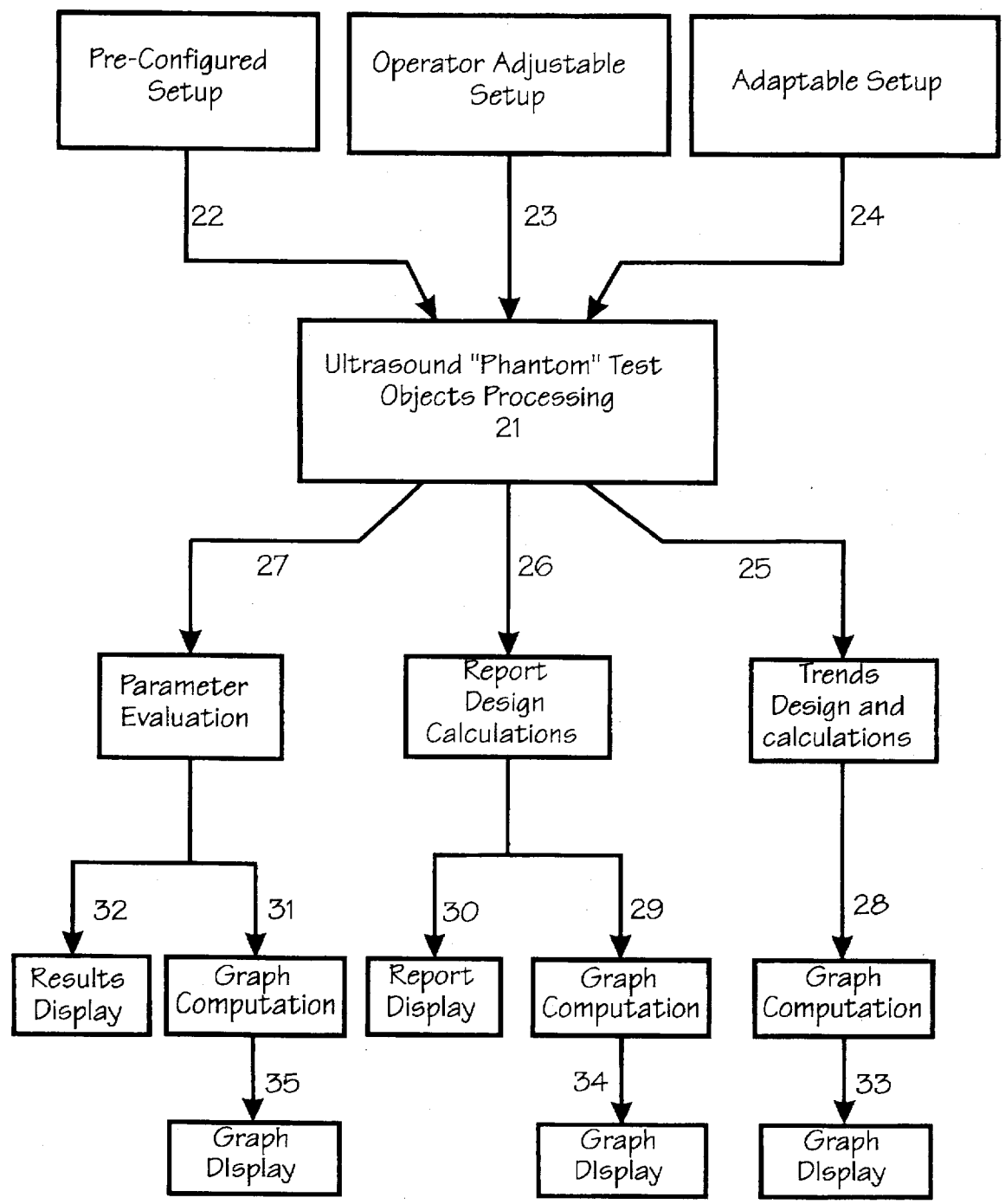
Figure 2. Processing of "Phantom Image"

Figure 3. Parameter Evaluation Procedure
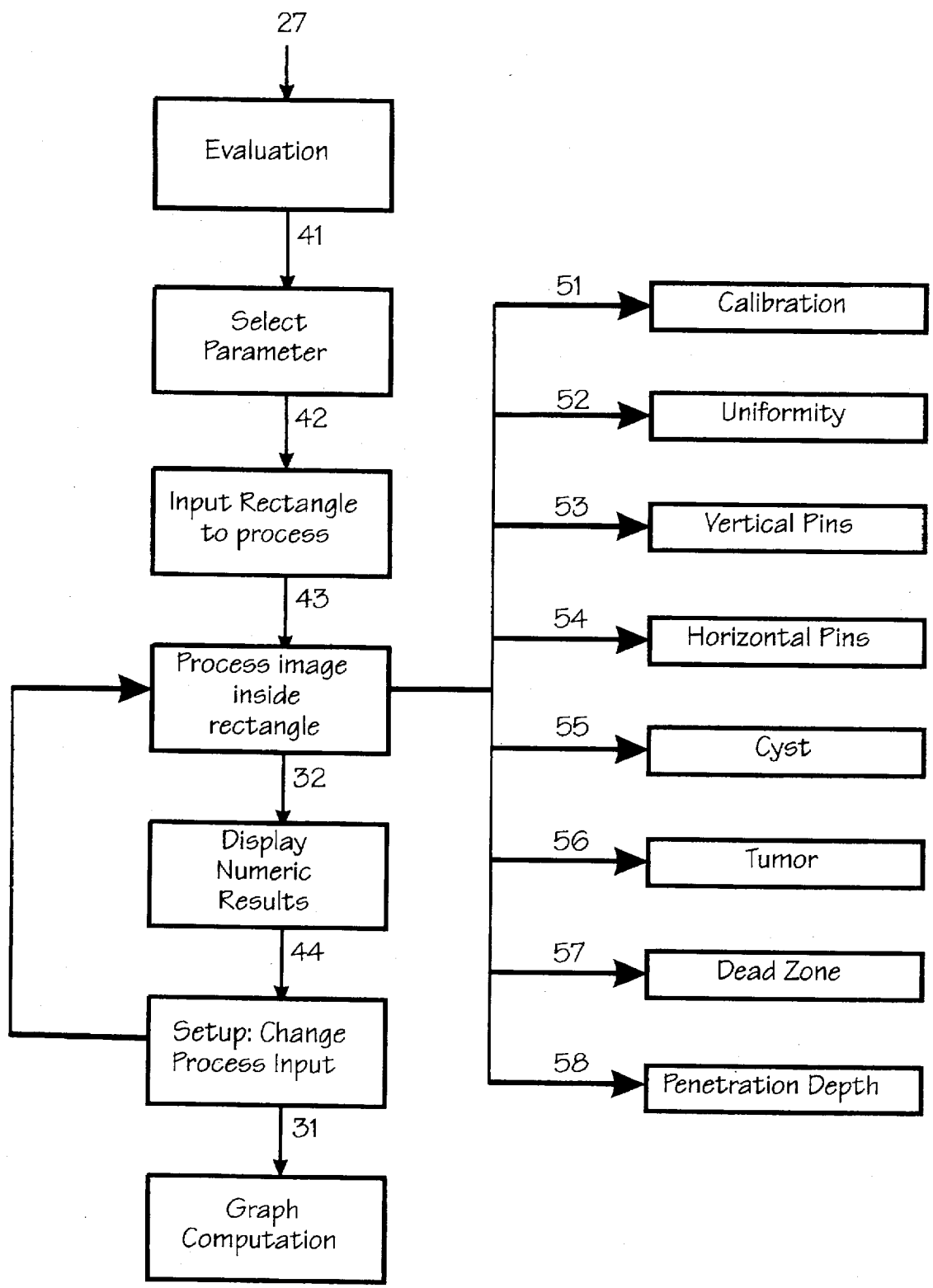

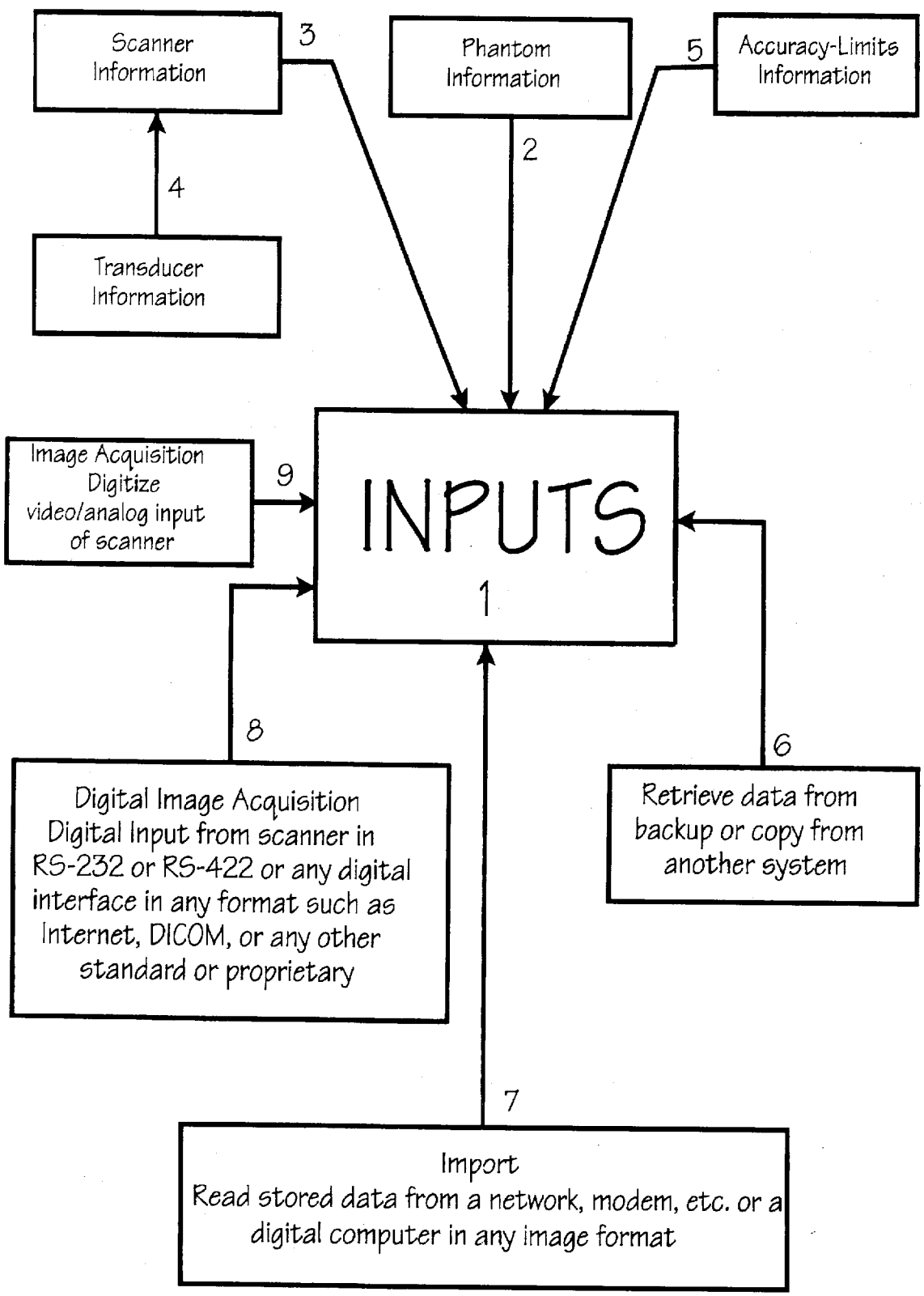
Figure 4. General Schematic-Inputs

Figure 5. Phantom Test Objects
Phantom 200
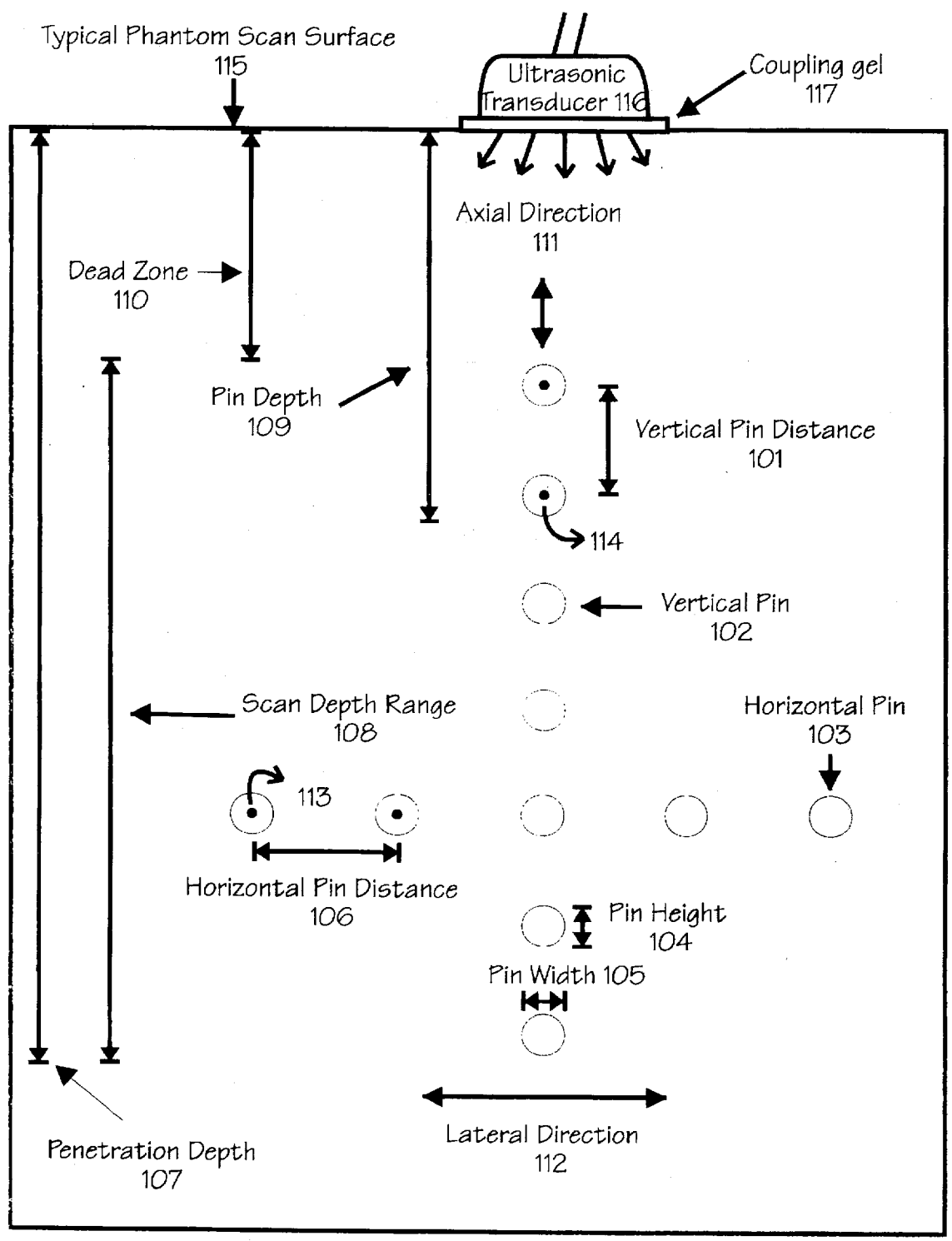

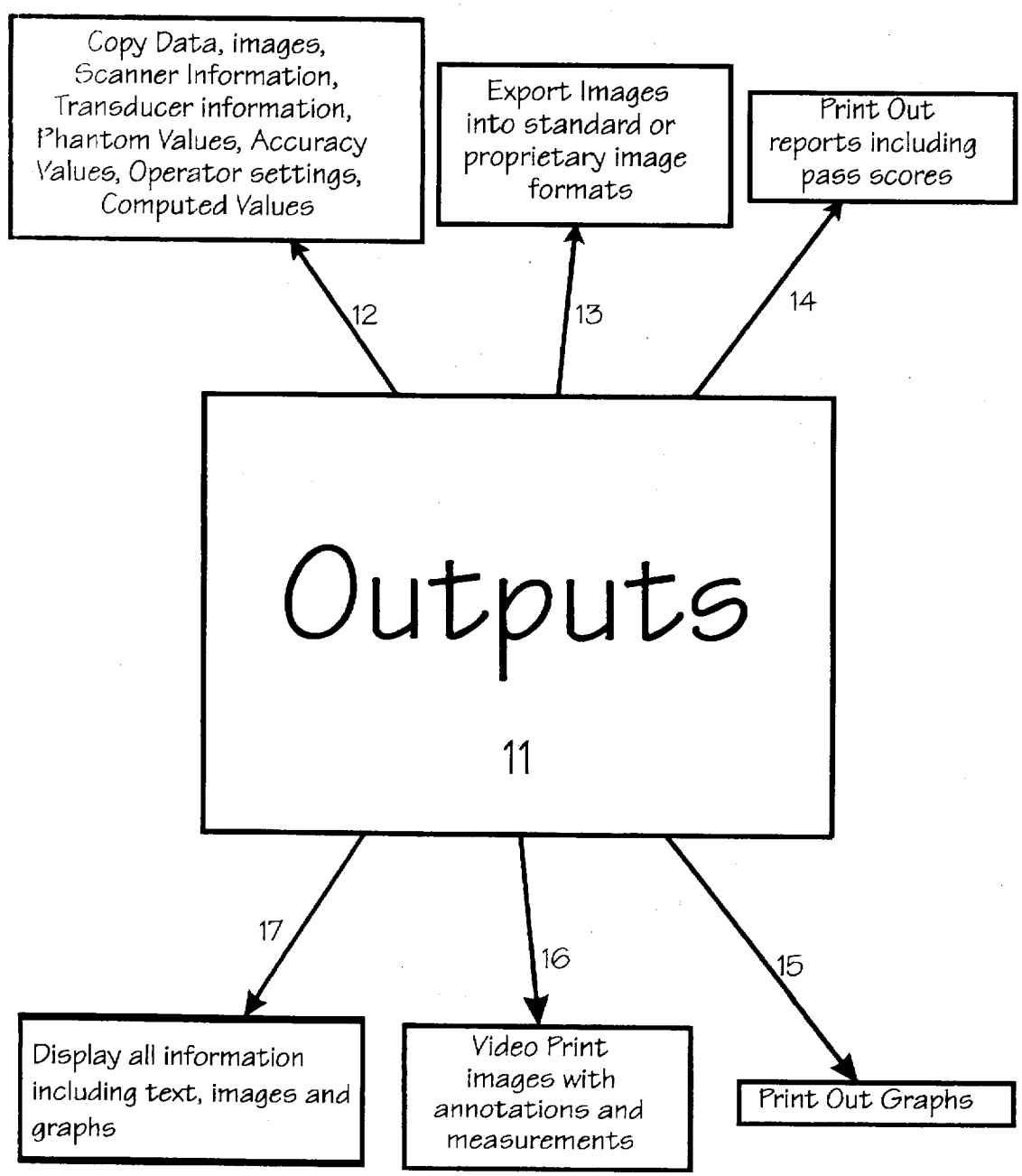
Figure 6. General Schematic-Outputs

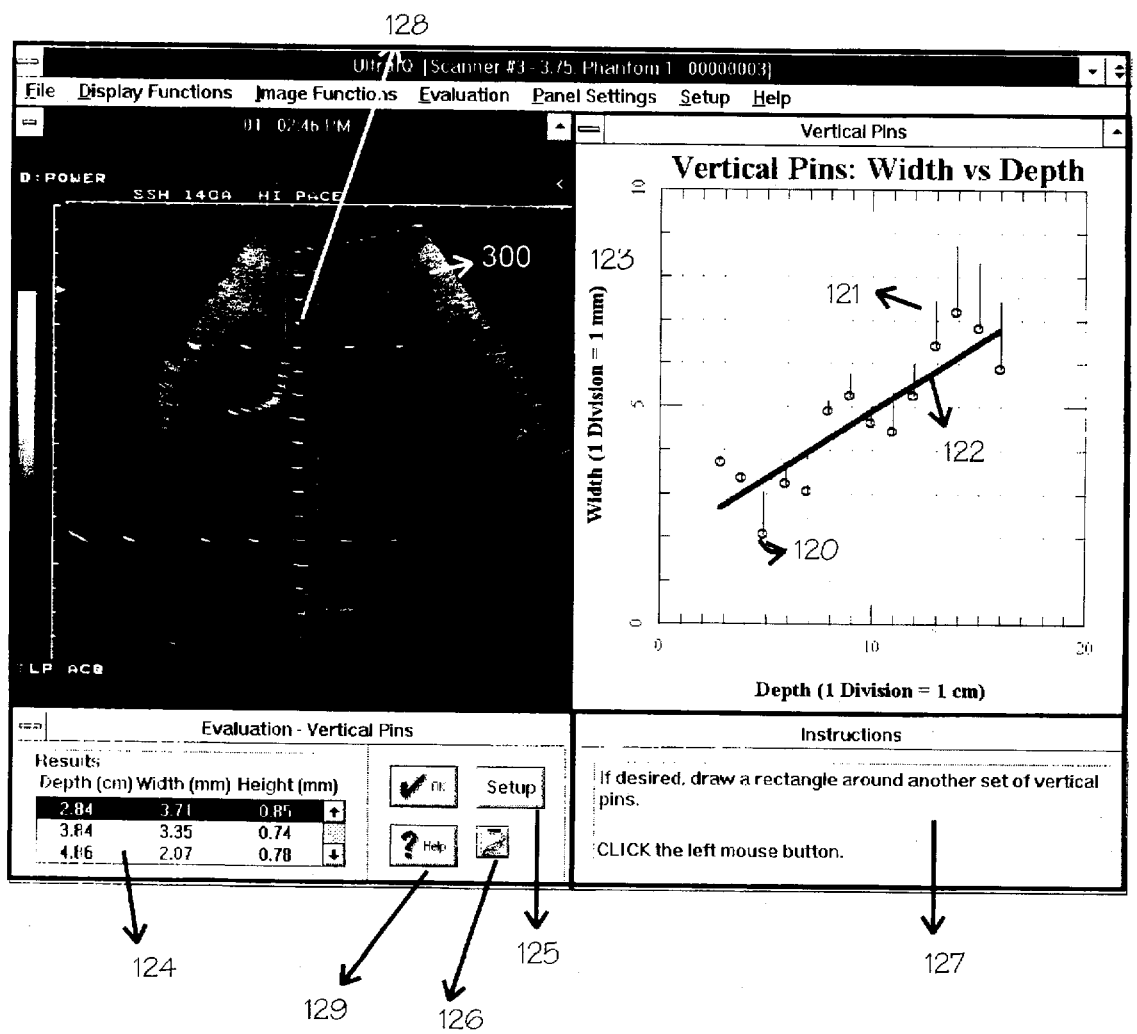
Figure 7: Display Example In Operation

Figure 8. Example of Object Profile
Pin Object Gray Level Profile in Axial Direction
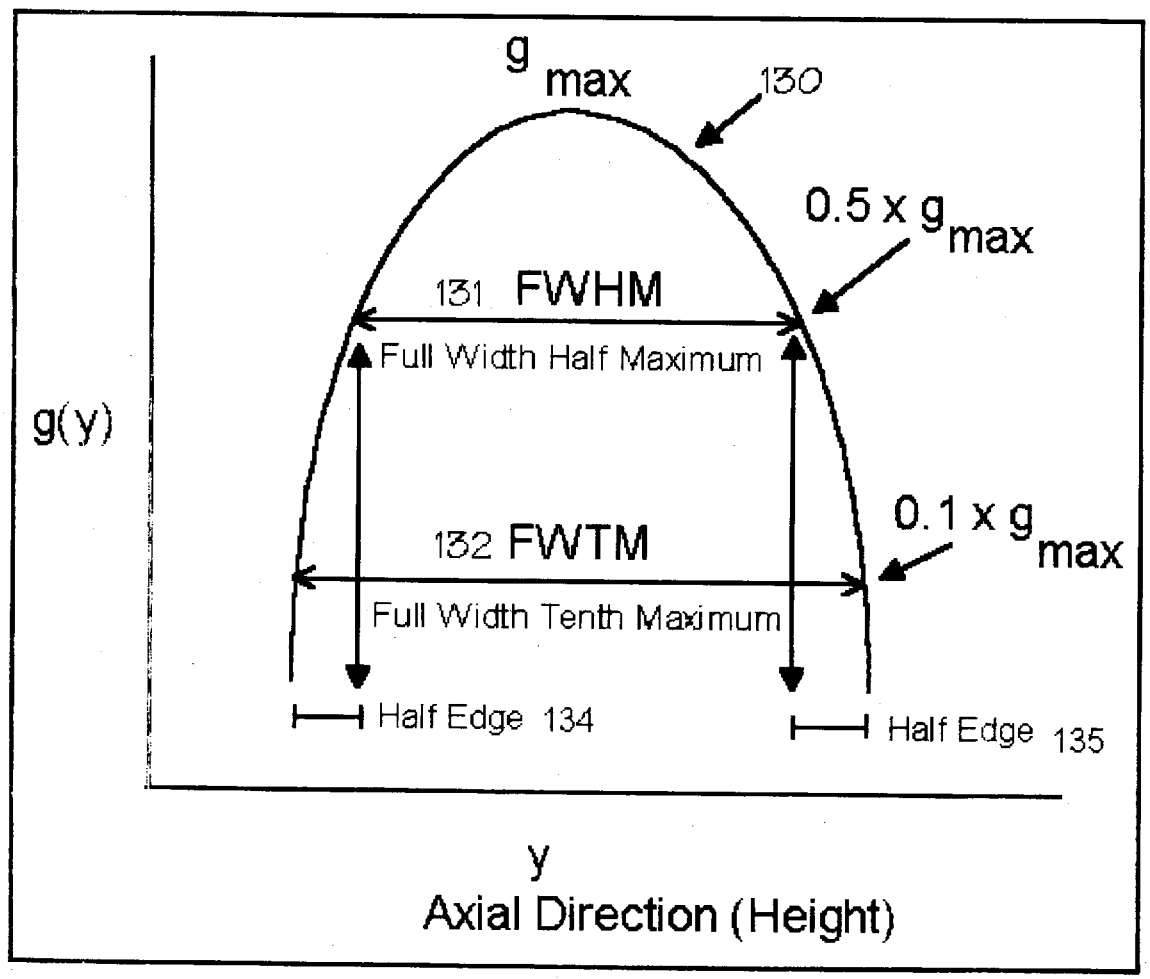

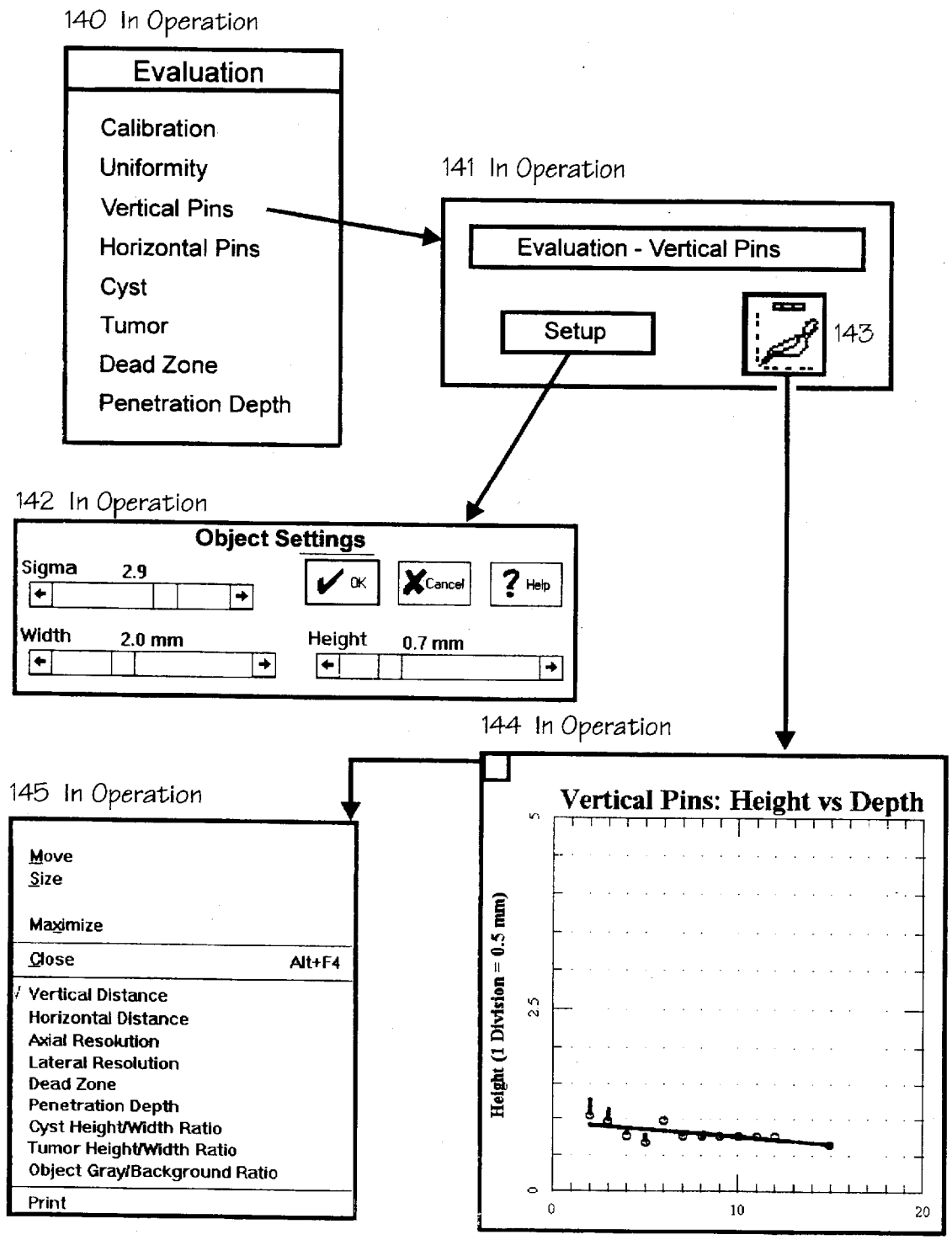
Figure 9. Typical Evaluation Operational Flow Chart

Figure 10. Typical Reports and Trends Operational Flow Chart
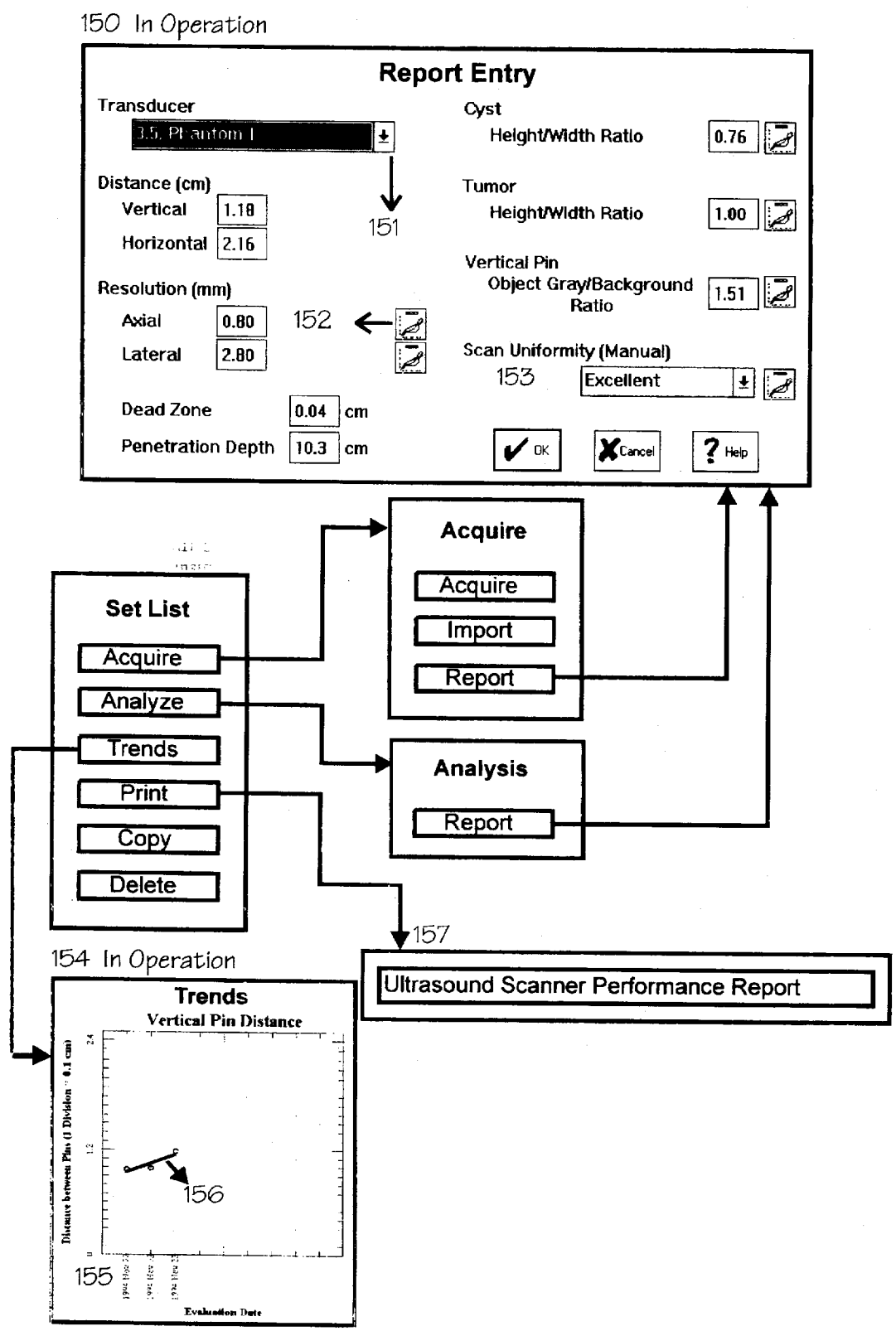

Figure 11. Typical Processing Menus
160 In Operation
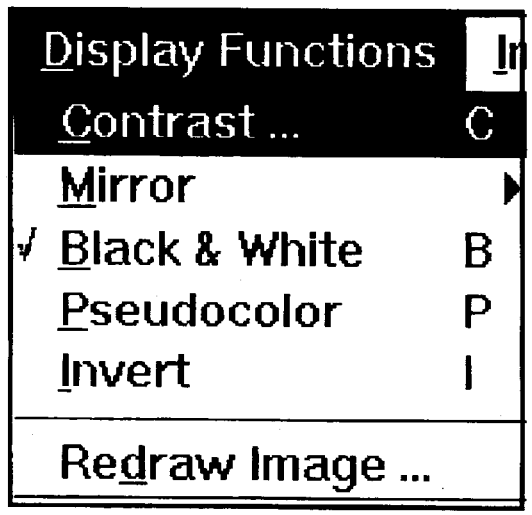
161 In Operation
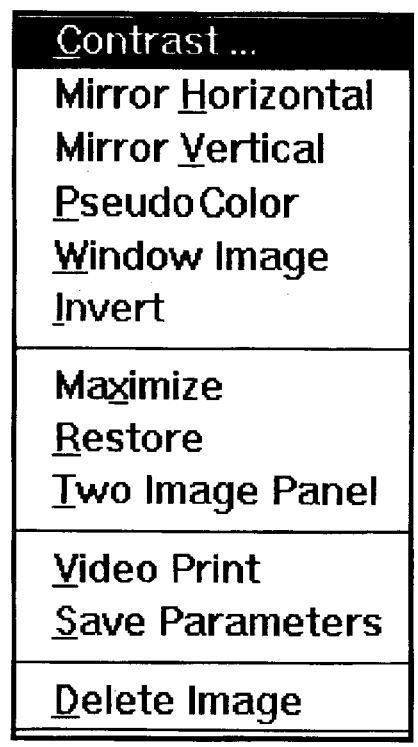
163 In Operation
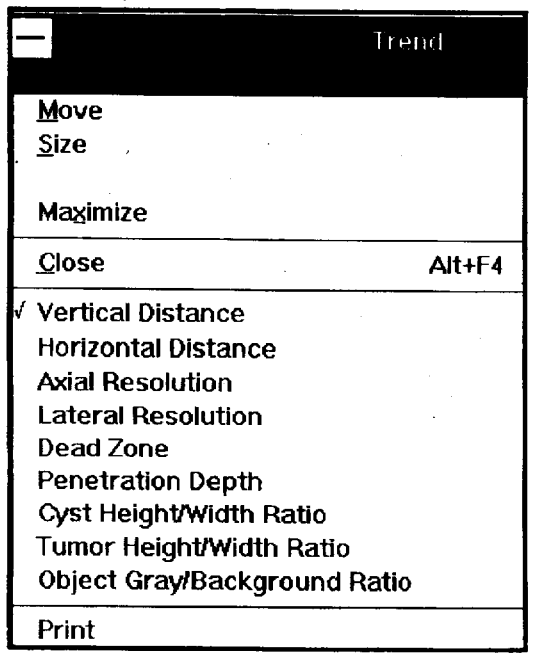
162 In Operation
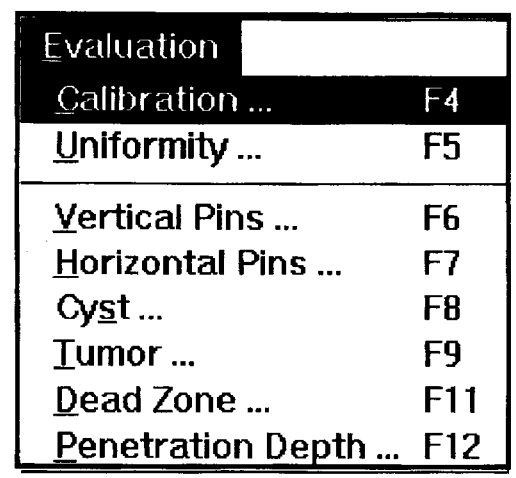

Figure 12: Typical Dialog for Database Access -- In Operation

Scanner/Transducer List

| Scanner | Location | Transducer |
|---|---|---|
| Scanner #1 | Missisauga | 3.5, Phantom 1 |
| Scanner #1 | Missisauga | 5.0, Phantom 1 |
| Scanner #1 | Missisauga | 7.5, Phantom 1 |
| Scanner #2 | Etobicoke | 3.5, Phantom 1 |
| Scanner #3 | Markham | 3.75, Phantom 1 |
| Scanner #3 | Markham | 7.5, Phantom 1 |
| Scanner #4 | Hamilton | 2.5, Phantom 2 |
| Scanner #4 | Hamilton | 3.75, Phantom 2 |
| Scanner #5 | Toronto | 3.5, Phantom 2 |

[ ✔ OK ]  [ Set List... ]  [ New Set ]  [ ? Help ]

[ Phantom ]  [ Limits ]  [ Update ]  [ Delete ]

Figure 13: Typical Dialog for Accessing Tasks -- Operation

Set List - Scanner #1

| Set Date | Set ID |
|---|---|
| 1994 Nov 22 | 00000001 |
| 1994 Nov 22 | 00000008 |
| 1994 Nov 22 | 00000009 |

[ ✔ OK ]
[ Acquire ]
[ Analyze ]
[ Trends ]
[ Print ]
[ Copy ]
[ Delete ]
[ ? Help ]

Figure 14. Typical Performance Parameters Entry Dialog In Operation

Phantom Values - Scanner # 1, 3.5, Phantom 1

Distance (cm)  Resolution (mm)
Vertical  [1]   Axial    [.5]   Dead Zone         [.4]  cm
Horizontal [1]  Lateral  [.8]   Penetration Depth [10]  cm Copy From
[Scanner #1, 3.5, Phantom 1  ▼]

[✔ OK]  [✘ Cancel]  [? Help]

Figure 15. Typical Performance Parameter Limits Entry Dialog - In Operation

Accuracy Values - Scanner #1, 3.5, Phantom 1

Distance                          Resolution
Vertical    ± [.10]  ⊙ mm ○ %    Axial   + [20]  ○ mm ⊙ %
Horizontal  ± [.15]  ⊙ mm ○ %    Lateral + [20]  ○ mm ⊙ %

[✔ OK]

Dead Zone + [3]  ⊙ mm    Penetration Depth - [5]  ○ mm
                 ○ %                              ⊙ %
                                                          [✘ Cancel]
Copy From
[Scanner #1, 3.5, Phantom 1                        ▼]
                                                          [? Help]

Figure 16. Ultrasound Scanner Performance Report

| Produced by | VIJAY RAMANATHAN | | | Date: 1995 Feb 20 | |
| --- | --- | --- | --- | --- | --- |
| Measurements by | VIJAY RAMANATHAN | | | Date: 1994 Nov 22 | |
| | | | | | |
| Scanner Name: | Scanner #3 | Serial # | S3 | | |
| Manufacturer: | Company C | Model # | A3 | | |
| Location: | Toronto | | | | |
| | | | | | |
| Transducer Name: | 3.75, Phantom 1 | Serial # | TRANS3.75 | | |
| Distance Accuracy: | Vertical Spacing | 1.01 cm | Horizontal Spacing | 2.12 | cm * |
| Spatial Resolution: | Axial | 0.83 mm | Lateral | 2.07 | mm |
| Scan Depth: | Dead Zone | 0.73 cm | Penetration Depth | 16.5 | cm |
| ObjectParameters: | Pin Object Mean Gray to Background Gray Ratio | | | 2.27 | |
| | Cyst Object Mean Height/Width Ratio | | | 0.93 | |
| | Tumor Object Mean Height/Width Ratio | | | 0.75 | |
| Scan Quality: | Uniformity/Artifacts | | | Excellent | |
| | | | | | |
| Transducer Name: | 7.5, Phantom 1 | Serial # | TRANS7.5 | | |
| Distance Accuracy: | Vertical Spacing | 0.99 cm | Horizontal Spacing | | |
| Spatial Resolution: | Axial | 0.72 mm | Lateral | 1.81 | mm |
| Scan Depth: | Dead Zone | 0.57 cm | Penetration Depth | 7.6 | cm |
| ObjectParameters: | Pin Object Mean Gray to Background Gray Ratio | | | 18.90 | |

\* - value to the left is outside acceptable range

UltraIQ Report - Page 1

Copyright © 1994-1995 RamSoft Inc.

METHOD AND APPARATUS FOR EVALUATING SCANNERS

FIELD OF THE INVENTION

The present invention relates to the evaluation of ultrasound images. In particular, the invention applies the processing of ultrasound scanner images for performance evaluation of scanner, transducers, phantoms and scan techniques; includes screen display and print out on paper of graphs, images, results and reports; includes storage, backup, copy and retrieval of all above information objects.

DISCUSSION OF BACKGROUND

An ultrasound image is produced by sending ultrasound pulses or waves of energy into a reflecting medium and collecting the reflected energy using specialized transducers applicable to clinical diagnostic imaging needs. Reflected energy is transformed into images, consisting of grayscale value at a depth and distance inside the medium. Shape and grayscale or halftone values of the image define the objects and background inside the medium. The image is frozen and displayed by a monitor connected to the ultrasound scanner. Scanner electronics output the image information as a standard video or in a digital format. Image output in video format is converted and saved into digital form by a frame grabber of sufficient quality. Image in digital format is read into processing computer memory and stored into hard drive or storage media. Image is displayed from computer (desktop, laptop or notebook) on a grayscale display screen or monitor.

Test objects made of tissue-mimicking materials called "ultrasound phantom" are available in the market to produce images to simulate liver tissues, cysts and tumors. In addition these include ultra-small high reflectance and low reflectance test objects to reveal fundamental instrument properties of ultrasound scanner system. Typical phantom objects are sketched in FIG. 5. The phantom is scanned using transducer 116, to produce images of the phantom test objects. Images are frozen and temporarily stored in scanner memory. In current quality assurance (QA) practice, these images are printed on a dedicated film camera using video output of the ultrasound scanner.

Subjective analysis is performed using the film image and results are manually documented to produce quality assurance reports. However, distance measurement for a selected object can be obtained, one at a time, with the aid of scanner's built in calipers, by visually selecting distances such as diameter of a phantom object such as vertical pin 102 on the scanner's display. Phantom objects are displayed as grayscale image, with as many as 256 shades between black and white. It is not possible to accurately determine spatial extent of such a displayed object by visual means. Current subjective methods do not permit any accurate verification of scanner imaging performance parameters either in production or operational settings.

It is important to evaluate scanner system as whole, including transducers, gain controls and imaging electronics from output image signals. Objective scanner quality performance evaluation is essential for manufacturing production line, quality assurance audit, for operational installations and for regular periodic maintenance. Quantitative performance evaluation is necessary to calibrate or service the scanner system after breakdowns to achieve reproducible imaging performance.

The present invention will be useful for: ultrasound scanner manufacturers; quality assurance professionals and consultants in industry; hospitals and clinics; and service engineers. Ultrasound images are used to diagnose several abnormalities or disease conditions in humans and animals. In industry, ultrasound imaging is used for nondestructive testing (NDT) of fluid filled pipes, cracks in welds of material joints etc.

The present invention is applicable to identify the actual variations in performance of a scanner system in relation to various methods of scanning, and variety of transducer designs. Thus, this apparatus is a valuable tool for research. Quality assurance methods are an integral part of any teaching programs in ultrasound imaging curriculum and quantitative approaches to performance evaluation will enhance knowledge of scanners.

Using a laptop or notebook computer hardware, will render this apparatus portable, convenient for evaluating scanners at different locations.

SUMMARY OF THE INVENTION

The present invention is an apparatus for evaluating an ultrasound scanner, comprising: a processor, a storage device, at least one output device, at least one input device; and software means operative on the processor for:

(a) maintaining in the storage device information on the scanner;

(b) maintaining in the storage device information regarding expected performance standards;

(c) maintaining in the storage device information regarding at least one phantom test object;

(d) inputting via said at least one input device;

(e) interactively specifying said at least one phantom test object in image for processing;

(f) processing said specified phantom test object in image to quantitatively determine the characteristics of said scanner;

(g) maintaining in the storage device results of said processing; and (h) outputting via said at least one output device results of said processing.

Software means incorporate methods of interactive and automatic evaluation of medical images to produce quantitative parameters, graphs, trends of parameters and reports related to the characteristics of image. The information stored and processed by software means consists of: (1) a database table to include information on ultrasound scanner and transducers, (2) a table to include information on the phantom (test object) design features, (3) a table to include expected performance standards information, (4) a means of storing and associating the images and the above tables or information, (5) a means of relating user provided and default processing information to images, and all of the above information, (6) a user interface that lets user process images for visual enhancement, permits to specify region of objects for processing, select type of evaluation and processing, vary processing parameters, select graphs, and hard copy outputs such as printout on paper and film, (7) a means to copy or retrieve, all information above, and (8) on-line help.

BRIEF DESCRIPTION OF THE DRAWINGS AND FIGURES

FIG. 1 is a schematic of an apparatus used for evaluating ultrasound scanner image quality by the present invention.

FIG. 2 is a flow chart depicting component steps involved in processing of phantom images by the present invention.

FIG. 3 is a flow chart of procedures of the present invention for evaluating characteristic parameters of ultrasound scanners by processing phantom objects.

FIG. 4 is a schematic of various information inputs of the present invention.

FIG. 5 is an illustration of typical ultrasound phantom consisting of test objects.

FIG. 6 is a schematic of various information outputs of the present invention.

FIG. 7 is an illustration of typical display output of the present invention in operation.

FIG. 8 is a sketch of a typical object gray value profile used for processing in the present invention.

FIG. 9 is a flow chart depicting typical evaluation procedures of the present invention in operation.

FIG. 10 is a flow chart consisting of typical reports and trends of the present invention in operation.

FIG. 11 is an illustration of typical processing menus of the present invention in operation.

FIG. 12 is an illustration of a typical dialog for accessing information databases of the present invention in operation.

FIG. 13 is an illustration of a typical dialog for accessing processing tasks of the present invention in operation.

FIG. 14 is an illustration of a typical dialog for data entry of expected ultrasound scanner performance parameters of the present invention in operation.

FIG. 15 is an illustration of a typical dialog for data entry of permissible accuracy or deviation of the expected ultrasound scanner performance parameters of the present invention in operation.

FIG. 16 is a hardcopy output of a typical ultrasound scanner performance report produced using the present invention in operation.

DETAILED DESCRIPTION OF THE INVENTION

The present apparatus in FIG. 1 acquires phantom images from scanner either by analog mode or digital mode.

Analog mode involves digitizing the video output 211 from scanner using video frame grabber or analog to digital converter hardware 204 and the digital image is transferred to memory of computer 207.

In digital mode of image acquisition, digital output 213 of the image information from the scanner's memory, with appropriate protocol, is read into processing computer memory via digital Input/Output port 205 of computer 207.

After the image of phantom objects is received into computer memory, the image is processed under user's control, producing numerical results, graphs, and reports automatically with specially designed and implemented algorithms. The results, graphs and reports are displayed on display 206 and can be printed using printer 210 connected to computer. The display subsystem 206 can be a CRT (cathode ray tube) monitor, or any of a variety of screen displays (such as Active or Passive Matrix) used with laptop, notebook, or sub-notebook computers. User communicates with processing computer 207 usually with mouse or trackball 209 and keyboard 208. The processed or unprocessed images can be sent to video printers or video film camera, available in the market, using video output 212 from video frame grabber 204.

The information inputs to the apparatus are displayed in FIG. 4. The outputs from the apparatus are given in FIG. 6. Image processing architecture is presented in FIG. 2. The apparatus uses graphic user interface consisting of dialogs, pull-down menus, buttons, on-line instructions and on-line help.

Ultrasound scanner test objects called "phantoms" are made of tissue-mimicking materials. Phantoms are commercially available to produce images simulating liver tissues, cysts and tumors. In addition, these include ultra-small high reflectance test objects, in FIG. 5, to determine fundamental imaging properties such as spatial resolution, of ultrasound scanners. Characteristics of these image objects are calculated using specific algorithms. Images are produced by scanning particular face 115 and inputted to processing computer by any of the methods of acquisition 8 or 9 in FIG. 4. Images can be retrieved 6 from stored information in FIG. 4 or imported 7 into this apparatus from different image and information storage formats.

The outputs are described schematically in FIG. 6. Apparatus offers facilities to copy 12 all of the data including images onto a digital media such as disk or tape or export 13 data in different digital formats. Ultrasound Performance Evaluation reports 14 can be printed out automatically for each scanner identifying every ultrasound transducer parameters individually. Reports also indicate whether the parameters fall outside the norm as specified in Accuracy-Limits information 5 and Phantom Information 2. All of the data and calculations are quite specific to each scanner and transducer as per tables Scanner Information 3 and associated Transducer Information 4.

The processing of the image covers the significant aspect of the invention. The processing of the test objects FIG. 5 contained in phantom images is illustrated in FIG. 2. Setup parameters for processing each class (type) of objects such as pins, cysts or tumors may consist of any one or a combination of pre-configured values 22, operator adjustable 23 using a graphic user interface 142, voice interface or any other computer peripheral input such as keyboard, pen, etc., or data dependent adaptable programmed setup 24. Processing of objects consists of three modes such as scanner performance parameters evaluation 27 for a particular image 140, calculations to produce performance report 26, 150 from all images of a test, and computations involving several tests of the same scanner equipment configuration 25 to analyze trends 163, 154 of any performance parameters over a period of time. From any one of these processing tasks, numerical results display 32, and 30, or 124, computation of graphs 31, 29, 28 and display of graphs 35, 34, 33 or 123, 144, 154 are provided. Any of these are accessible from evaluation dialog window 126, 152 or other set list window FIG. 13. All windows provide help button to explain objects in the window and on-line help accesses all definitions, descriptions, procedure explanations, and "How To . . ." accomplish a particular operation. Help is also accessible by pressing F1 key.

The important features of the present invention include (i) methods and implementation of calculation of test object parameters as in 51–58 (ii) procedure, implementation and display of direct and derived parameters in graphs, (iii) implementation of analysis of trends from different sets of measurements (iv) interactive and pre-configured adjustments of parameters (v) automatic and manual reports using expected values of parameters and permissible range of value deviations. Features, advantages and applications of the present invention will be apparent to those skilled in the art from a careful reading of the detailed description presented below and accompanied drawings, formulas, definitions and examples.

Calibration 51 of vertical and horizontal distances are performed in axial direction 111 and lateral direction 112 relative to the scan surface 115. Distances are calculated from user inputs, preset values or prestored values of unit relationship in each direction for number of pixels per unit distance (cm, mm etc.) giving slope and an image (pixel) position where absolute value is given to specify intercept. The calibration is done for each image, or values from any set can be used for other or all images by user prompt without need for calculation for every image.

Evaluation of uniformity object 52 consists of basic method for analyzing test objects in following steps: (i) select an area of interest in image, in which there are no test objects (this is referred to as background) and which covers as much vertical distance and horizontal distance as possible, provided by user input, pre-configured, or prestored, (example 128, selected rectangular shape for vertical pins in operation) and (ii) select a suitable cell size in terms of number pixels and center for calculating weighted mean and standard deviation as per formula given below or any equivalent method. Several variations of implementations are possible using various computational cell dimensions depending on the frequency of ultrasound transducer, material of the phantom (tissue characteristics) and weighted mean of pixel gray values inside the computational cell using different weighting schemes.

A two dimensional grayscale image consists of discrete picture elements called pixels arranged in columns and rows. Each pixel in image has a grayscale value, a specific discrete shade value between black and white. Gray shade value of a pixel is referred to as gray value. Mean gray value computed for a number of pixels in a selected region is called mean gray. Statistical fluctuations of gray values of pixels in the selected regions can be calculated with respect to mean gray.

Evaluation of uniformity 52 characteristics yields, for a given phantom design, fluctuations in gray value and mean gray value at different depths within a selected region, in the direction of the beam 111 or at different positions in the direction perpendicular to the beam 112. In practice, this is essential to assess total image noise, including that of scanner electronics and transducer signals. Drifts and fluctuations of gray values in image performance can be quickly assessed with the present procedure and appropriate corrective actions can be taken. An important consideration here is that the uniformity parameters are calculated and displayed in graphs for all the depths or horizontal positions of the phantom. Thus, any nonlinear electronic variations are identifiable. Unless there is an enormous change in fluctuations, it is not possible to identify this problem with the current qualitative Quality Assurance (QA) procedures. When films are used for visual evaluations, film recording method itself may modify the image uniformity. If grayscale fluctuations in image increase, degree of visual definition of image objects decreases. If grayscale fluctuations decrease, image objects are smoothed out reducing the ability to identify small objects or spatial resolution. Any variations from baseline performance requires attention. In clinical images this situation could affect the diagnosis.

Let us denote vertical or axial (or ultrasound beam) direction with y and lateral direction with X, orthogonal to beam direction, following x–y Cartesian coordinate system.

If $U(x,y,\rho)$ is a gray scale distribution of the image at any pixel $P(x,y)$, the mean value of the gray value of uniformity object $<g>_U$ is calculated as $$<g>_U = \Sigma_{x,y}\{U(x,y,\rho)W(\rho)\}/N \quad \text{(equation 1)}$$

for every pixel included in the defined region where N is the total number of pixels and $W(\rho)$ is a normalized weighting function;

this could depend on a number of parameters such as depth, sector angle or horizontal position, tissue material, transducer frequency, TGC controls etc. The standard deviation $\sigma_U$ is given by $$\sigma_U = \sqrt{\Sigma(<g> - U(x,y,\rho))^2/(N-1)} \quad \text{(equation 2)}$$

for all (x,y) in the computational cell included in the rectangle.

Depth refers to the vertical distance measured in an image using the calibration in the axial (beam propagation) direction from the top of the phantom or scan surface.

All the calculated values for each image are stored in object classes. Typical graphs associated with uniformity object are:

(i) Mean Gray with respect to Depth with error bars displayed by $\pm\sigma_U$ and (ii) Sigma Ratio $\sigma_U(d)/<g(d)>_U$ with respect to Depth d.

These values are computed to provide instant display of results.

Uniformity object is computed in axial 111 and lateral 112 directions. Results from uniformity object are used to detect other objects.

Vertical pin objects are designed vertically down from the scanning surface to evaluate image properties in the direction of the beam or axial direction 111 as in FIG. 5. The scanned image appears in operation as displayed in FIG. 7 with vertical pin objects marked 128. These pin objects in phantom images are brighter than the background or the gray level of these objects are higher than the uniform background gray level. Usually, the diameter of these objects are (about 0.3 mm–0.1 mm) considerably smaller than the minimum resolvable object diameters or axial resolution of typical scanners. Vertical pin objects 102 are processed to evaluate several performance parameters such as pin object height 104, pin width 105, pin-to-pin distance 101, and pin depth 109. Evaluation 53 of vertical pin objects uses results from uniformity calculations 52. Object detection is based on object settings 142 or setup parameters as per methods 22–24.

Horizontal pin objects 103 are designed parallel to the scanning surface 115 to evaluate the image properties in the lateral or perpendicular direction to the scanning beam. Usually, the number of horizontal pins are fewer than vertical pins. Vertical and horizontal pins are scanned from the same face and the image includes both type of pins. In some phantoms, there may be sets of horizontal pins at several depths.

These pin objects are designed across at fixed depths from the scanning surface to evaluate image properties in the lateral direction. Horizontal pin objects in phantom images are brighter than the background or the mean gray of these objects are higher than the mean background gray. Usually the diameter of these objects are (about 0.1 mm) considerably smaller than the axial resolution of typical scanners. Horizontal pin objects 103 are processed to evaluate several performance parameters such as pin object height 104, pin width 105, pin-to-pin distance 106, and pin depth 109. Evaluation 54 of Horizontal pin objects uses results from uniformity calculations 52. Object detection is based on object settings 142 or setup parameters as per methods 22–24.

Analysis of vertical 53 and horizontal 54 pins in image yields (i) measurement of pin distance and spacing between imaged pins in axial 101 and lateral 106 directions to verify accuracy of scanner electronic caliper measurements, (ii) minimum resolvable object sizes or diameters 120 in each direction for whole depth or horizontal positions of the phantom, (iii) mean grayscale of objects, (iv) fluctuations of grayscale within pin objects, (v) ratio of fluctuations to mean gray value of objects, (vi) area of objects in each direction for whole depth or horizontal positions of the phantom, (vii) extent of object edges 121 in each direction for the whole depth or horizontal positions of the phantom, and (viii) ratio of pin objects mean gray to mean gray value of background giving how well pin objects are imaged with respect to background.

Benefits of the above results are several fold: (i) Verification of scanner differential distance calibration throughout axial and lateral positions, which is important for clinical size measurements. Without the present apparatus this measurement is not feasible for scanners in operational environments. (ii) Systematic analysis of object diameters and edges at different depths or horizontal positions permits understanding or verification of important physical parameters such as scanner spatial resolution and focal zone. It is well known that spatial resolution of ultrasound scans are different in axial and lateral directions. Object diameters and edges vary with depth and horizontal position. The calculated values are displayed in graphical form as 123 in operation. By inspecting this graph or other graphs readily available to user, any deviations from normal results or abnormalities of performance can be identified and necessary action can be taken immediately. By noting that the object diameters and edges are minimum at the focal zone, scanner's focal zone settings can be verified from viewing corresponding graph 123. (iii) Systematic examination of object mean gray provides insight into power attenuation with depth and behaviour of gain controls. Ratio of object fluctuations of grayscale to mean gray value, yields gain independent parameters. This graph depicts object "noise" to object signal ratio. Any spurious deviations observed from these graphs indicate imaging system problems or drifts warranting action. Best fit curve drawn in graph is helpful in pinpointing the variations easily. (iv) Systematic inspection of ratio of object mean gray value to background mean gray gives a measure of contrast of object against background under same scanning conditions. Object contrast is fundamental to the purpose of image scanning for detection of objects and diagnosis based on image.

In current practice, such precise and detailed systematic measurements and graphs are not feasible, even though these values are crucial in imaging performance assessment. The present invention provides these insightful results automatically.

Vertical and horizontal pin diameters in phantom must be appreciably smaller than resultant object image diameters for the above considerations. As the scanner technology improves, pin image object diameters would become smaller requiring different pin designs. It is noticeable, from image in example 128, pin objects become elliptical indicating object diameters are different in axial and lateral directions. Lateral diameter of pin is larger than or equal to axial diameter. Pin objects in phantom are circular by design. Thus it is evident, object image shape obtained by scanning is not exact representation of original object. This characteristic is important in evaluation of cyst and tumor objects.

Cyst (anechoic, very low reflectance objects or darker than background) 300 and tumor (echoic, brighter than background or very high reflectance objects) in phantom are designed with criteria that their sizes are considerably larger than pin image object diameters. These phantom objects are designed to produce different preset reflectance at a particular ultrasound frequency. These simulate objects of diagnostic clinical investigations. Evaluation of cyst 55 and tumor 56 is important to understand clinical imaging capability in terms of geometry, contrast, and noise. Processing of cyst and tumor objects offers following results: (i) Diameters of objects in axial and lateral directions, (if) Ratio of axial diameter to lateral diameter for each object, (iii) Area of each object in each direction, (iv) Mean gray and fluctuations from mean gray of each object in every direction, and (v) Ratio of fluctuations to mean gray for every object in each direction. Advantages of the above performance characteristic are to achieve: (i) Quantitative estimate of shape asymmetry, (if) Relative variations of object mean gray in relation to predesigned reflectance parameters, in other words, how well relative reflectance are imaged in terms of grayscale, and (iii) Object "noise" or fluctuations.

Baseline values for each transducer and scanner combination can be established by initial measurements and deviations can be monitored for corrective action. If a manufacturer can provide "factory" values of the parameters, using these as baseline values, measurements at the installation site can be verified. Periodic performance measurements can be compared against installation baselines. Any appreciable deviations can be corrected by service engineering and performance baseline levels can be restored. Thus, this invention helps scanner imaging performance to be maintained in a reproducible manner. In addition, complete documentation is produced, test data saved and long term trends of scanner performance parameters are also available automatically for inspection.

Detection is implemented based on pixel gray value, minimum required size of object, and other parameters based on tissue characteristics. Algorithm for object detection is given below.

For bright objects such as vertical pins, horizontal pins, and tumors, find object such that pixel gray value $P(x,y,\rho)$ $$P(x,y,\rho) \geq <g>_U + n \cdot \sigma_U; \qquad \text{(equation 3)}$$

For dark objects such as cyst, find object such that pixel gray value $P(x,y,\rho)$ $$P(x,y,\rho) \leq <g>_U - n \cdot \sigma_U; \qquad \text{(equation 4)}$$

where n is any rational positive value, usually between 1.0 and 3.0, set by 22–24 or 142. Additional criteria can be imposed by object settings 142 on the object based on height $\Delta y$ vertical extent or extent in the axial direction 111 and $\Delta X$ horizontal extent or extent in the lateral direction 112 or value of tissue characteristics $\rho$.

Mean gray and standard deviation are calculated for all phantom objects, such as vertical pins, horizontal pins, cysts, and tumors using equations 1 and 2.

Gray value profile $G(y)$ of the object in axial direction 130 is computed for the object by summing pixel gray values in the orthogonal direction $$G(y) = \Sigma_x P(x,y,\rho) \text{ inside the object.} \qquad \text{(equation 5)}$$

Distribution using equation 5 gives axial line spread function of the scanner. Functional dependence of $\rho$ is omitted for simplicity.

Gray value profile $G(x)$ of the object in the lateral direction is written as $$G(x) = \Sigma_y P(x,y,\rho) \text{ inside the object.} \qquad \text{(equation 6)}$$

Distribution using equation 6 gives lateral line spread function of the scanner.

Object height $h_2 = |Y_+ - Y_-|$
where at $$y = Y_{30} \text{ and } y = Y_-, \text{ the value } G(y) = G_{maximum}/2.0 \quad \text{(equation 7)}$$

and

Object height $h_{10} = |Y'_+ - Y'_-|$, where at $y = Y'_+$ and $y = Y'_-$, $$G(y) = G_{maximum}/10.0 \quad \text{(equation 8)}$$

Object width $W_2 = |X_+ - X_-|$
where at $x = X_+$ and $x$ $$= X_- \text{ the value } G(x) = G_{maximum}/2.0 \quad \text{(equation 9)}$$

Object width $W_{10} = |X'_+ - X'_-|$
where at $x = X'_+$ and $$x = X'_- \text{ the value } G(x) = G_{maximum}/10.0 \quad \text{(equation 10)}$$

The values $h_2$ and $W_2$ are referred to as Full-Width-Half-Maximum (FWHM). The values $h_{10}$ and $W_{10}$ are referred to as Full-Width-Tenth-Maximum (FWTM). Axial diameter of object is given by $h_2$ and lateral diameter is $W_2$.

Object edge is defined by $\epsilon_A = h_{10} - h_2$ in axial direction and $\epsilon_L = W_{10} - W_2$ in lateral direction. Object is sharp and well defined in axial direction when $\epsilon_A \cong 0$. Profile calculation and parameters deduced from profile of ultrasound image objects is a basic component of the present invention.

Using object profile, then following object characteristics are determined: (i) geometric center or centroid 113 or 114, (ii) axial "diameter" or object height $h_2$ 131 of the object 104 as per equation 7 and lateral diameter object width $W_2$ 105 as per equation 9 and (iii) the object edges 134, 135 of the object $\epsilon_A$ in axial and $\epsilon_L$ lateral directions as per equation 8 and equation 10 respectively. Currently marketed test objects are circular and we evaluate "diameters". However, present method of object analysis is designed for any object shape. Diameter in any designated direction is defined as a distance between two points on the profile having a specific ratio to the peak value on the object profile. We have, for specificity, used Full-Width-Half-Maximum (FWHM) 131 for diameter 120 as defined in equations above. Implementing edge calculation $\epsilon_A$ and $\epsilon_L$ is one of the important features of this invention. Object edge (sum of 134 and 135) is displayed in typical graph 123 as a vertical line 121. Equivalent calculations can be implemented either using profile or traditional edge enhancement and edge extraction procedures. The display of edge 121 and object height (axial diameter) or object width 120 (lateral diameters) with depth of the object demonstrates systematic behaviour of spatial resolution the scanner. Thus, the calculation and display of edge 121 in a typical graph 123 is another key feature of the present invention. Several performance interpretations are derivable from profile evaluation and extraction of "diameter" and "edge" information through equivalent methods to achieve similar results and display. The edge and diameter, together, are important in establishing focal zone of the transducer, in terms of numerical results and graph display 123. This feature is an important result of this invention. All graphs are produced for visual display on screen, printout on paper or film, or digital export to other programs. Performance characteristics evaluation the following pin and horizontal pin objects are described in the following paragraphs.

Distance calibration accuracy is calculated in axial direction 111 as vertical inter-pin distance 101 between centers of adjacent pins 114 and in lateral direction 112 as horizontal inter-pin distance 106 between centers of adjacent pins 113. A graph of vertical pin distance 101 with respect to depth (pin center) yields axial distance accuracy within the scan depth. A graph horizontal pin distance 106 with respect to depth (pin center) yields lateral distance accuracy within the scan width.

Using calibration values and object analysis as described above, object area, object mean gray, and standard deviation are calculated for every object. Display graphs are provided with respect to object depth for vertical pin object area, and vertical pin object mean gray, with standard deviation from mean gray of the object. The area of the object is obtained by counting the number of pixels inside the object boundary and multiplying by calibration factors.

From these values, ratio of pin object mean gray to background (uniformity) mean gray at that depth, is evaluated. This ratio represents a performance parameter related to object contrast and independent of the operator settings of the scanner such as power, TGC etc. Another deduced ratio, of standard deviation to mean gray of the pin object is evaluated as well. This ratio is a measure of object "noise" to object signal for the pin object. Graph of this ratio for objects at different depths depicts depth dependence of object noise.

These values are produced for each object and graphs are produced for all parameters described for every depth as in graph 123 or every horizontal position. Object contrast can be defined in several ways. The present invention enables automatic evaluation and provides quantitative results for objects at every depth for display and print out.

The analysis described above is performed for vertical pins 102 appearing in axial direction 111 and horizontal pins 103 in lateral direction 112. There is no restriction that the objects be aligned in any direction. Vertical pin objects produce graphs with respect to depth and Horizontal pin objects display graphs with respect to horizontal position.

Objects are processed inside selected region in image. No restrictions are placed on size or position of selected region. Processing procedure is not limited to a particular shape of defining area, ie. rectangle as long as objects are inside. If objects are not detected, processing can be redone by varying object settings 142 using setup 125.

The object parameters are analyzed using curve fitting techniques (such as least squares) for finding and displaying 122 systematic variations of performance characteristics in every graph. Numerical results 124, for example, are also presented.

With every menu or procedure, operational instructions 127 are provided on the screen to help user. More detailed Help is typically accessible through button 129 in each dialog, by pressing F1 key or accessing Help menu. Automatic operational instructions 127 integrated with operational menu or dialog, together with context sensitive Help buttons 129, are user interface aspects of the present invention.

The above description applies to evaluation of vertical and horizontal pins. Typical evaluation menu in operation is presented in 162. From above calculations and results, performance parameters axial resolution and lateral resolution of ultrasound scanner are evaluated for report production.

Several equivalent definitions for axial resolutions are possible, all depending on the spatial extent of the object in axial direction, minimum or mean. Basically, this parameter defines ultrasound scanner's ability to detect and clearly display closely spaced objects that are placed in axial direction. Axial resolution is determined by identifying the closest two pins designed for axial resolution determination. Smallest separation between pin objects that can be perceived at each depth is recorded as the axial resolution. Pin objects are considered separate when a dark line is seen between them as displayed.

The above definition applies to visual identification of objects and does not take into account gray scale variations (profile) of pin object from end-to-end in axial direction. We have extended this definition to estimate precisely the "diameters" in axial and lateral directions using the characteristics of the pin objects. Our method produces numerical results automatically, which is a fundamental aspect of this invention.

The axial resolution is calculated as the mean value of all vertical pin heights $h_2$ from all images for the transducer in a particular set. The axial resolution from other methods may provide slightly different values. The evaluation method applied here provides a mathematical basis for establishment of consistent baseline values and comparisons.

Lateral resolution defines the scanner's capability to discriminate adjacent objects perpendicular to the axial direction. Lateral resolution is evaluated by measuring the width of pin objects $W_2$ at different depths (near, mid or far field zones of the transducer). Currently, calipers available with scanner are used to measure the width of a pin object in the focal zone based on the visual display associated with the scanner. This current method is subjective and does not lend itself, to precise measurement. With this approach, it is not practical to measure widths at different depths. The present invention permits quantitative and automatic evaluation of heights and widths for every object in image.

The lateral resolution is calculated as the minimum value of all vertical pin widths $W_2$ from all images for the transducer in the particular set. The variation of width with object depth is displayed in a typical graph in example, Vertical Pin Width vs Depth graph 123; the edge value is drawn as a vertical bar from value of diameter. It is observed from measurements that object edges in lateral direction are usually considerably higher than in the axial direction.

Cyst objects 300 are anechoic objects producing pixel gray values lower than mean gray of uniformity objects. Object detection is performed using equation 4. Usually, cyst objects are larger in size than pin objects. All parameters evaluated for pin objects are computed for cyst objects. In addition, ratio of height to width (or axial diameter to lateral diameter) of objects is also available as a measure of performance.

Cyst objects provide graphs of ratio of height to width with respect to depth and with respect to position to indicate the imaging capability of the scanner in terms of object geometry. This is important for clinical size measurements. Graphs, for cyst area, mean gray, and ratio of standard deviation to cyst mean gray for each object, with respect to depth and lateral position are provided for instant understanding of imaging performance of cyst objects.

Tumor objects are echoic objects producing pixel gray values higher than mean gray value of uniformity objects. Object detection is performed using equation 3. Usually tumor objects are larger in size by design than pin objects. All parameters evaluated for pin objects are computed for tumor objects as well. In addition, ratio of height to width (or axial diameter to lateral diameter) of objects is also available as a measure of performance.

Tumor objects provide graphs of ratio of height to width with respect to depth and with respect to position to indicate the imaging capability of the scanner in terms of object geometry. This is important for clinical size measurements. Graphs, for tumor area, mean gray, and ratio of standard deviation of tumor mean gray to tumor mean gray value for each object, with respect to depth and lateral position are provided for inspecting imaging performance of tumor objects.

All calculated parameters from each image for each transducer per measurement set are stored for further analysis and preparation of reports. To produce reports, results of calculations from all images of a set of measurements are used. Typical report dialog in operation is illustrated in 150. Data for every transducer for the scanner is accessible by using combo-dialog 151. Distance accuracy values are included in report. If processed values fall outside the phantom (design) performance values FIG. 14 and performance parameter limits FIG. 15, an asterisk is placed automatically to indicate the unacceptable performance score. Similar indication is provided in Typical Ultrasound Scanner Performance Report illustrated in FIG. 16. Axial and Lateral resolutions are calculated, as per definitions, using all images for each transducer of the set. Graphs for pin heights and widths including data from all images are accessible by clicking typical graph buttons 152. These graphs are quite different from graphs available from evaluation/results dialog 126 which include results from only one current image. Report for the transducer includes mean value of ratio of cyst height to width for all cyst objects, mean value of ratio of tumor height to width for all tumor objects, and mean value of pin objects mean gray to uniformity object mean gray value. Each of these parameters have associated graphs from results of all images.

Dead zone sketched as 110 in FIG. 5, is the vertical distance down from scan surface, no useful image information is seen. Dead zone is a result of interface between transducer and phantom material. Dead zone 57 is evaluated using operator input and distance calibration values, for any number of images. Dead zone parameter in report is maximum of all values from images of a set. This value of depth represents the minimum depth from which useful image information can be extracted. This value can be different for different phantom models or manufacturers depending on the material medium.

Penetration Depth 107 in FIG. 5, is the maximum depth beyond which no useful image information is available. Due to attenuation ultrasound waves in the medium beyond this depth no echo is received. Penetration Depth 58 is evaluated based on user input and distance calibration values, for any number of images. Penetration Depth parameter in report is arrived at as the minimum of all values from images of a set. This value represents the maximum useful depth from the scanning surface. This value can be different for different phantom models or manufacturers depending on the material medium.

The vertical distance from dead zone to penetration depth is useful scan depth range 108 within which all objects of scan should be placed for any useful scan information. These parameters are significant in that the deviations affect visualization of clinically useful diagnostic object placements. The vertical distance from Dead Zone to Penetration Depth gives the clinical depth range. Any variations in the depth range require close inspection.

One more parameter included in the report is a subjective operator assessment of scan uniformity or scan quality 153 by user entry into combo-edit box or select on of precoded words such as Excellent, Good, or Poor.

A significant aspect of report dialog 150 in operation, is that the values are automatically produced except user assessment of Scan Uniformity 153. In addition, in circumstances when no acquired images are available, the user can enter values manually as well, if necessary. Thus, report dialog 150 permits manual and automatic entry of values. This facility is another practical feature of the present invention.

Automatic printed version of report 157 is enabled using Print button and typical report is illustrated in FIG. 16. Date of report production, reporter's name, date of measurement, name of measurement performer, Scanner related information, and parameters with test score (note for asterisk) evaluated for each transducer are printed.

Analysis of Trends is illustrated via graph 154 in operation. The data from several sets of previous measurements by dates 155 for the same scanner and transducer combination is analyzed to produce trend evaluation of the parameters over a period of time. The values 156 are analyzed using curve fitting techniques (such as least squares) to display deviations and direction of variation. Trend Graphs, useful for insight, documentation and service, are also a key aspect of the invention. Trend Graphs for all report parameters are accessible from Trend menu 163 in operation, accessible from any trend graph and trend button.

Images are accessed from database elements specific to particular scanner, transducer, and measurement set; within the same measurement set, data of other transducers for the same scanner is accessible. From any graph 144, other graphs 145 related to the same object measurements are accessible. Inter-accessibility of scanner database, images, graphs and report and trends is a basic aspect of the invention yielding a user friendly apparatus.

Typical image manipulations using Display Functions menu 160 in operation, for all images of a set are available from menu as illustrated. Individual image manipulations are also possible with menu such as 161 in operation, from each image. Other display functions (different image formats such one, two, eight, magnification both fixed and variable) lending to user desired viewing of images.

It will be apparent to those skilled in the art that many changes and substitutions, in definitions, equations, method, implementation, user interface, display or report, can be made to the present invention without departing from the spirit and scope as defined by the appended claims.

What is claimed is:

1. An apparatus for quantitatively evaluating image quality of an ultrasound scanner, comprising:
   a processor;
   a storage device;
   at least one output device;
   at least one input device; and
   software means operative on the processor for:
   (a) maintaining in the storage device information on the scanner;
   (b) maintaining in the storage device information regarding expected performance standards;
   (c) maintaining in the storage device information regarding at least one phantom test object;
   (d) inputting via said at least one input device;
   (e) interactively specifying said at least one phantom test object in image for processing;
   (f) processing said specified phantom test object in image to quantitatively determine image quality characteristics of said scanner to evaluate the scanner for diagnostic purposes;
   (g) maintaining in the storage device results of said processing; and
   (h) outputting via said at least one output device results of said processing.

2. The apparatus of claim 1, said software means further interactively allows for selection of a region in image with said phantom test object for analysis.

3. The apparatus of claim 1, said software means further interactively allows for setting object processing parameters and limits for analysis.

4. The apparatus of claim 1, wherein said output device is a printer.

5. The apparatus of claim 1, wherein said output device is a display screen.

6. A method of quantitatively evaluating image quality characteristics of an ultrasound scanner, comprising the steps of:
   (a) selecting a phantom test object within an image;
   (b) quantitative processing of said image to evaluate image quality characteristics of the scanner for diagnostic purposes; and
   (c) outputting results of the quantitative processing.

7. The method of claim 6, wherein said step of selecting an image involves selecting a region of said phantom test object.

8. The method of claim 6, wherein said quantitative processing includes evaluating object profile of said phantom test object in axial and lateral directions.

9. The method of claim 6, wherein said quantitative processing includes evaluating calibration.

10. The method of claim 6, wherein said quantitative processing includes evaluating uniformity.

11. The method of claim 6, wherein said quantitative processing includes evaluating vertical pin objects.

12. The method of claim 6, wherein said quantitative processing includes evaluating horizontal pin objects.

13. The method of claim 6, wherein said quantitative processing includes evaluating cyst objects.

14. The method of claim 6, wherein said quantitative processing includes evaluating tumor objects.

15. The method of claim 6, wherein said quantitative processing includes evaluating distance accuracy in axial and lateral directions.

16. The method of claim 6, wherein said quantitative processing includes evaluating dead zone and penetration depth.

17. The method of claim 6, wherein said outputting the analysis includes the compliance of processed results with stored performance standards.

18. The method of claim 6, wherein said outputting the analysis includes trends of processed results from several sets of tests.

19. The method of claim 6, wherein said quantitative processing includes evaluating at least one of:
   (a) said phantom test object diameter in axial and lateral directions;
   (b) said phantom test object edge in axial and lateral directions;
   (c) said phantom test object center;
   (d) said phantom test object area;
   (e) said phantom test object mean gray value; and
   (f) fluctuations in said phantom test object mean gray value.

20. The method of claim 6, wherein said quantitative processing includes evaluating distance between said phantom test objects in axial and lateral directions.

* * * * *